US012171857B2

(12) United States Patent
Choi et al.

(10) Patent No.: US 12,171,857 B2
(45) Date of Patent: Dec. 24, 2024

(54) CELL PENETRATING PEPTIDES AND USES THEREOF

(71) Applicant: Kan Zen Co., Ltd, Seoul (KR)

(72) Inventors: Won Sup Choi, Seoul (KR); Hyun Sun Park, Uiwang-si (KR); Da Som Kwon, Seoul (KR); Tae Kyu Park, Seoul (KR)

(73) Assignee: Kan Zen Co., Ltd, Seoul (KR)

( * ) Notice: Subject to any disclaimer, the term of this patent is extended or adjusted under 35 U.S.C. 154(b) by 862 days.

(21) Appl. No.: 17/292,005

(22) PCT Filed: Nov. 19, 2020

(86) PCT No.: PCT/KR2020/016357
§ 371 (c)(1),
(2) Date: May 7, 2021

(87) PCT Pub. No.: WO2021/112458
PCT Pub. Date: Jun. 10, 2021

(65) Prior Publication Data
US 2022/0304913 A1    Sep. 29, 2022

(30) Foreign Application Priority Data

Dec. 6, 2019    (KR) .................. 10-2019-0161346
Dec. 6, 2019    (KR) .................. 10-2020-0099210

(51) Int. Cl.
*C07K 7/06*    (2006.01)
*A61K 8/64*    (2006.01)
*A61Q 19/00*   (2006.01)
*C07K 7/08*    (2006.01)
*C07K 14/33*   (2006.01)

(52) U.S. Cl.
CPC .............. *A61K 8/64* (2013.01); *A61Q 19/00* (2013.01); *C07K 7/06* (2013.01); *C07K 7/08* (2013.01); *C07K 14/33* (2013.01)

(58) Field of Classification Search
CPC . A61K 8/64; A61Q 19/00; C07K 7/06; C07K 7/08; C07K 14/33
See application file for complete search history.

(56) References Cited

U.S. PATENT DOCUMENTS

| 7,192,596 B2 | 3/2007 | Shone et al. |
| 2017/0246266 A1 | 8/2017 | Lee et al. |
| 2019/0055285 A1 | 2/2019 | Choi et al. |

FOREIGN PATENT DOCUMENTS

| KR | 10-1254004 B1 | 4/2013 |
| KR | 10-2015-0139035 A | 12/2015 |
| KR | 10-2017-0031068 A | 3/2017 |
| WO | 2015-183044 A1 | 12/2015 |

OTHER PUBLICATIONS

UnitProt Accession No. A0A6G1BY54, accessed Jul. 9, 2024 at URL rest.uniprot.org/uniprotkb/A0A6G1BY54.txt (Year: 2024).*
UniProt Accession No. A0A9D5CT28 accessed Oct. 20, 2024 at URL rest.uniprot.org/uniprotkb/A0A9D5CT28.txt (Year: 2024).*
UniProt Accession No. A0A7N2KZG8 accessed Oct. 20, 2024 at URL rest.uniprot.org/uniprotkb/A0A7N2KZG8.txt (Year: 2024).*
International Search Report for PCT/KR2020/016357 mailed Feb. 25, 2021 from Korean Intellectual Property Office.
Parvaneh Saffarian et al., "Topical Botulinum Toxin: A Non-invasive Way for Treatment of Muscle Disorders", Current Drug Delivery, 2018, vol. 15, pp. 1375-1380.
Parvaneh Saffarian et al., "TAT-BoNT/A(1-448), a novel fusion protein as a therapeutic agent: analysis of transcutaneous delivery and enzyme activity", Applied Microbial and Biotechnology, 2016, 100:2785-2795.

* cited by examiner

*Primary Examiner* — Julie Ha
*Assistant Examiner* — Kristina M Hellman
(74) *Attorney, Agent, or Firm* — Revolution IP, PLLC

(57) ABSTRACT

The present disclosure relates to novel cell penetrating peptides and their applications in cosmetic compositions. These compositions include cell penetrating botulinum toxin recombinant proteins, which are fusion proteins of the cell-penetrating peptides and botulinum toxin. Also disclosed are polynucleotides encoding these recombinant proteins and recombinant expression vectors comprising these polynucleotides. The cell penetrating botulinum toxin recombinant proteins serve as active ingredients in the cosmetic compositions.

12 Claims, 7 Drawing Sheets
Specification includes a Sequence Listing.

[FIG. 1]
| NAME | SVMscore | Prediction | Hydrophobicity | Hydropathicity | Amphipathicity | Hydrophilicity | Mol wt |
|---|---|---|---|---|---|---|---|
| CDP4 | 1.74 | CPP | -1.02 | -2.47 | 1.79 | 8 | 1572.07 |
| CDP5 | 1.53 | CPP | -0.83 | -1.78 | 1.39 | 7 | 1529.05 |
| CDP3 | 1.52 | CPP | -0.74 | -1.13 | 0.99 | 6 | 1542.05 |
| CDP6 | 1.5 | CPP | -0.85 | -2.17 | 1.26 | 7 | 1602.1 |
| CDP7 | 1.43 | CPP | -0.68 | -1.08 | 0.99 | 6 | 1514.04 |
| CDP8 | 1.41 | CPP | -0.75 | -1.33 | 0.93 | 6.5 | 1592.12 |
| CDP9 | 1.39 | CPP | -0.78 | -1.72 | 1.1 | 6.5 | 1538.02 |
| CDP10 | 1.39 | CPP | -0.72 | -1.56 | 1.03 | 6.5 | 1548.05 |
| CDP11 | 1.35 | CPP | -0.73 | -1.32 | 0.95 | 6.5 | 1594.13 |
| CDP12 | 1.31 | CPP | -0.62 | -1.03 | 0.7 | 5.5 | 1523.01 |
| CDP13 | 1.3 | CPP | -0.57 | -0.61 | 0.7 | 5 | 1456.94 |
| CDP1 | 1.28 | CPP | -0.8 | -2.03 | 1.56 | 1.41 | 1356.8 |
| CDP2 | 1.27 | CPP | -0.68 | -1.22 | 1.56 | 0.82 | 1518.07 |
| 8R | 1.23 | CPP | -1.76 | -4.5 | 2.45 | 3 | 1267.6 |
| TAT | 1.07 | CPP | -1.21 | -3.64 | 2.12 | 1.99 | 1559.99 |
| Pep-1 | 1 | CPP | -0.39 | -2.04 | 0.37 | 3 | 2848.57 |
| IMT-P8 | 0.76 | CPP | -1.05 | -2.93 | 1.47 | 1.14 | 2274.84 |
| VP22 | 0.55 | CPP | -0.79 | -2.19 | 1.45 | 6.5 | 2190.78 |
| TD1 | -0.15 | Non-CPP | -0.13 | 0 | -0.3 | 2 | 1537.07 |
| MPG | -0.39 | Non-CPP | 0.26 | 1.33 | -0.81 | 0 | 1541.05 |
[FIG. 2]
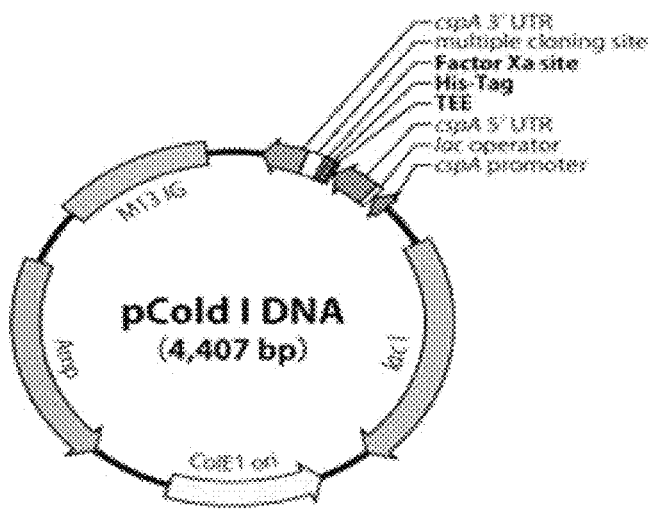

[FIG. 3]
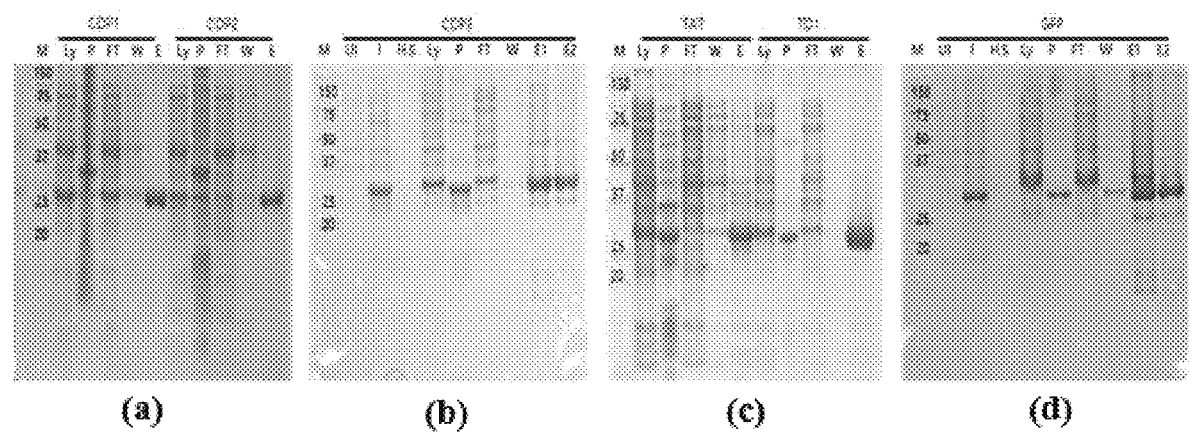
[FIG. 4]
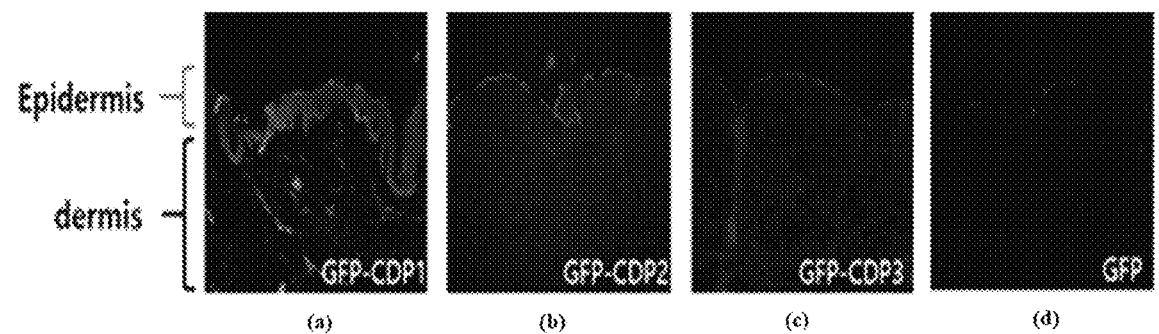

[FIG. 5]
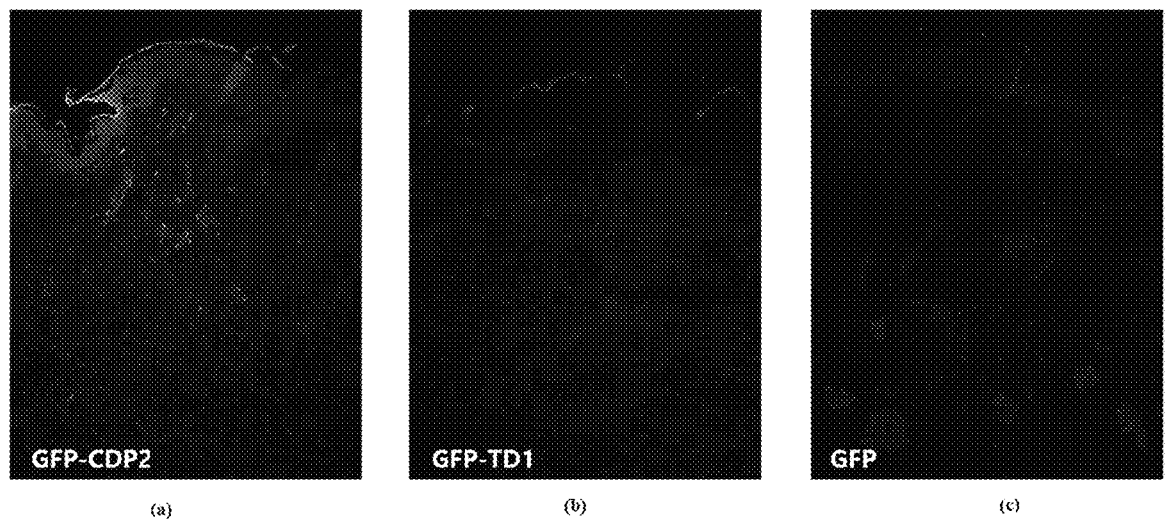
[FIG. 6]
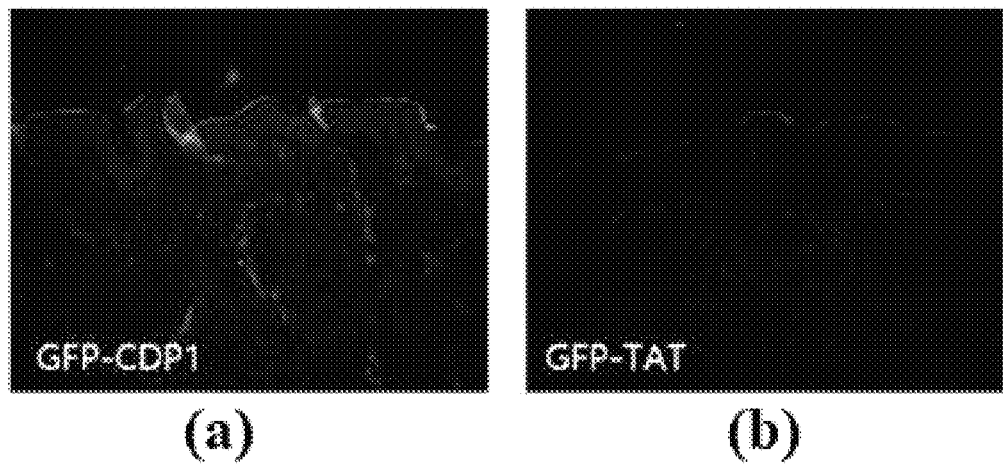

[FIG. 7]
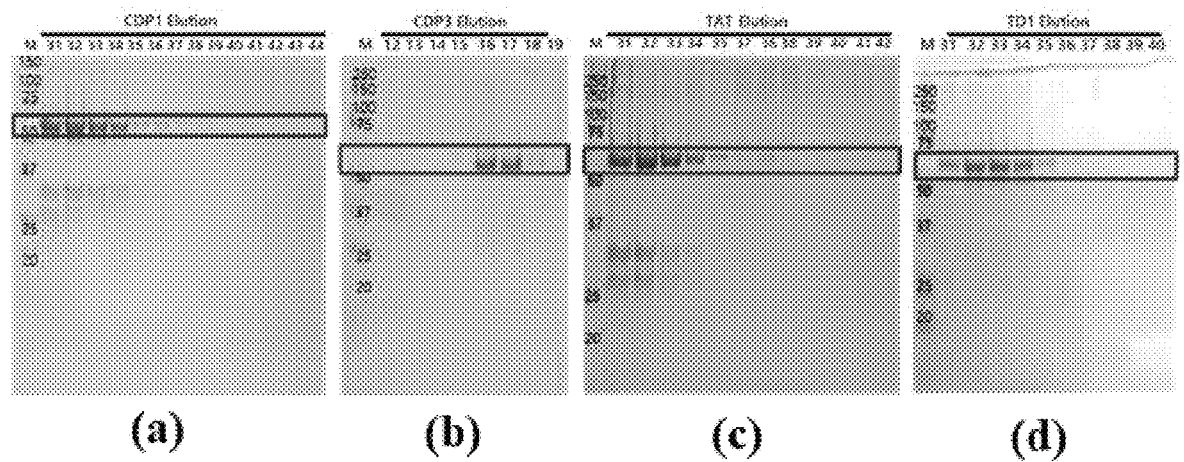
[FIG. 8]
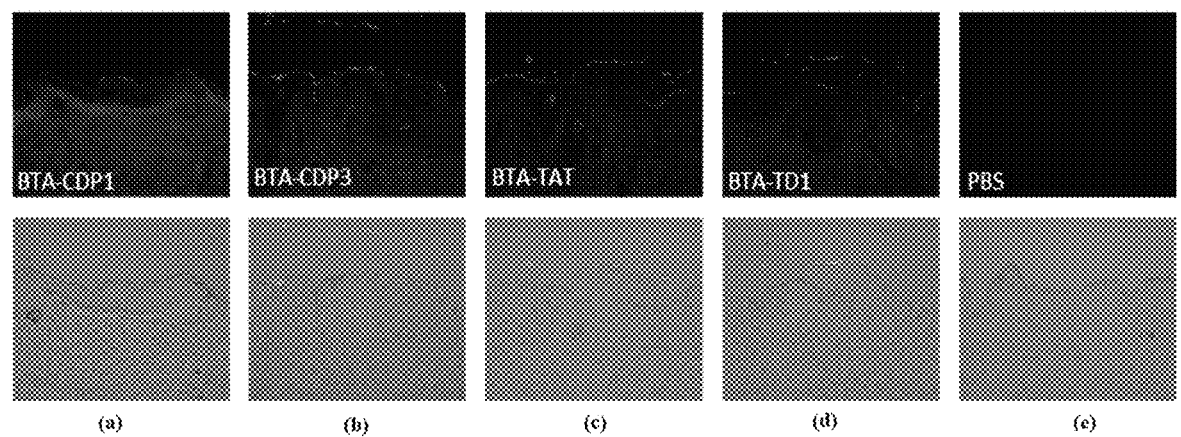

[FIG. 9]
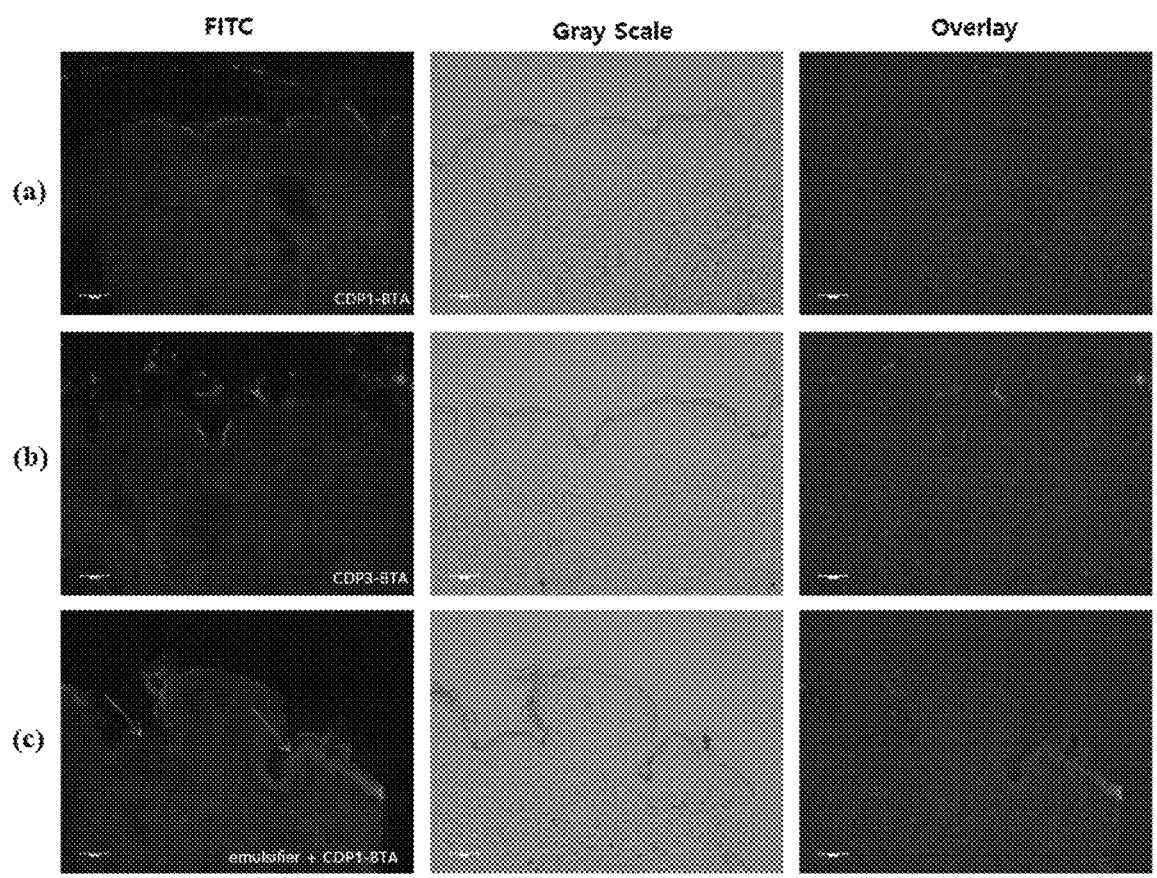

[FIG. 10]
| | Optical density with blank | | | | | Cell viability(%)_10% WST-1 media | | | | |
|---|---|---|---|---|---|---|---|---|---|---|
| Sample | 1 | 2 | 3 | 4 | | 1 | 2 | 3 | 4 | |
| Blank(10% WST-1) | 0.201 | 0.202 | 0.209 | 0.194 | 0.202 | | | - | | |
| TCPS | 0.549 | 0.477 | 0.453 | 0.499 | 0.495 | 99 | 100 | 100 | 101 | 100.000 |
| 5 µg/mL | 0.487 | 0.500 | 0.496 | 0.515 | 0.500 | 97.44 | 101.88 | 100.51 | 107.00 | 101.71 |
| 10 µg/mL | 0.511 | 0.512 | 0.515 | 0.513 | 0.513 | 105.63 | 105.97 | 107.00 | 106.31 | 106.23 |
| 20 µg/mL | 0.515 | 0.531 | 0.504 | 0.523 | 0.518 | 107.00 | 112.46 | 103.24 | 109.73 | 10.11 |
| 40 µg/mL | 0.503 | 0.459 | 0.464 | 0.511 | 0.484 | 102.90 | 87.88 | 89.59 | 105.83 | 96.50 |
| 80 µg/mL | 0.494 | 0.464 | 0.476 | 0.476 | 0.478 | 99.83 | 89.59 | 93.69 | 93.69 | 94.20 |
[FIG. 11]
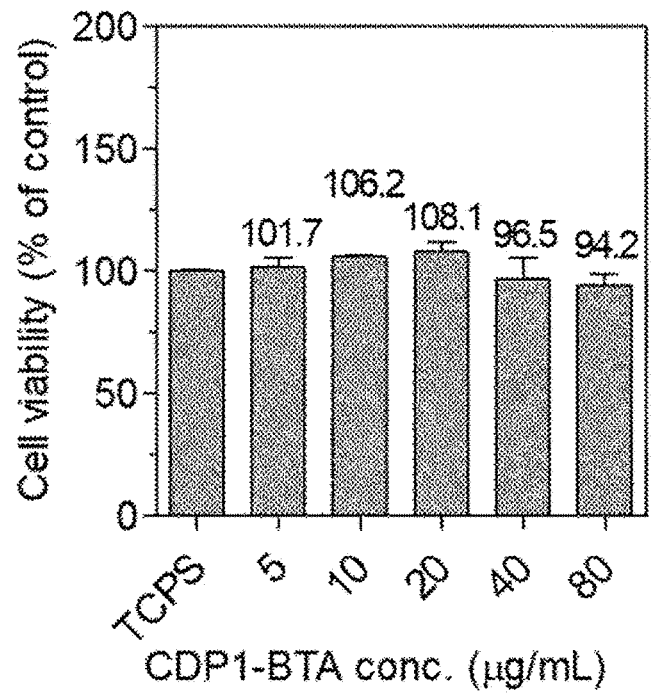

[FIG. 12]
| Time | Blank | BTA-Lc | BTA-CDP1 | BTA-CDP3 | BTA-TAT | BTA-TD1 |
|---|---|---|---|---|---|---|
| 0 | 37.184 | 46.733 | 57.376 | 66.745 | 50.761 | 60.193 |
| 15 | 35.085 | 69.537 | 92.559 | 129.133 | 64.846 | 101.472 |
| 30 | 29.836 | 127.756 | 126.890 | 167.593 | 86.246 | 137.503 |
| 45 | 29.046 | 177.871 | 152.864 | 192.651 | 104.258 | 161.198 |
| 60 | 31.294 | 199.742 | 169.924 | 206.813 | 118.986 | 183.145 |
| 75 | 28.252 | 207.541 | 186.331 | 213.467 | 131.090 | 189.488 |
| 90 | 26.819 | 199.926 | 192.662 | 212.540 | 141.241 | 199.084 |
| 105 | 28.052 | 206.947 | 195.233 | 217.462 | 157.141 | 202.626 |
| 120 | 29.798 | 209.180 | 206.098 | 217.718 | 162.766 | 208.273 |
| 135 | 30.626 | 209.558 | 208.189 | 222.596 | 170.708 | 208.592 |
[FIG. 13]
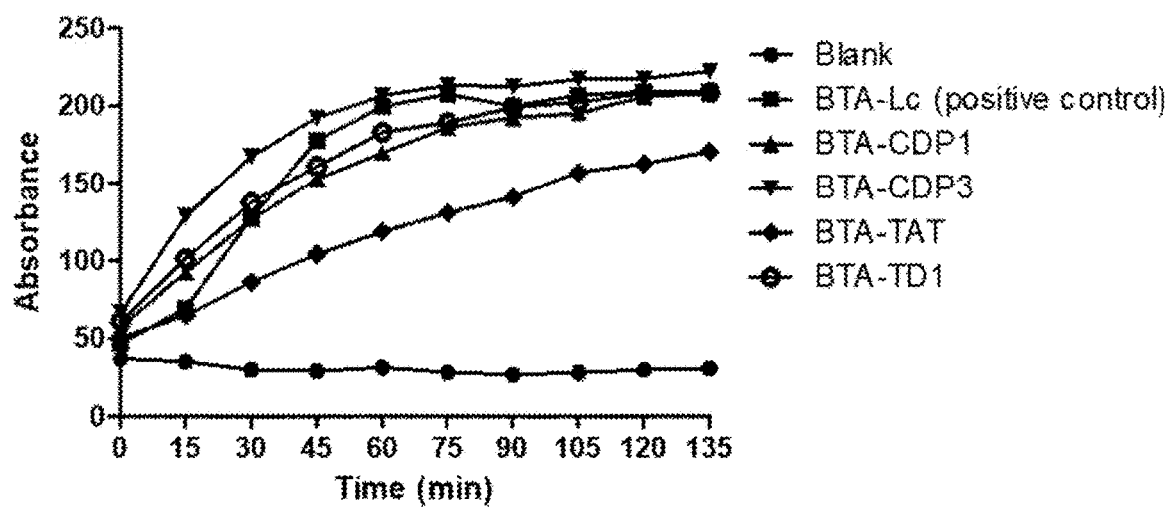

SEQUENCE LISTING

```
<160> NUMBER OF SEQ ID NOS: 28

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1
```

```
Gly Lys Arg Ser Arg Leu Arg Lys Pro Arg Cys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Cys Arg Ile Trp Arg Leu Arg Lys Arg Lys Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Gly Leu Arg Ile Arg Arg Leu Arg Arg Arg Ser Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Gly Leu Arg Arg Arg Arg Lys Arg Lys Arg Ser Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Gly Leu Arg Lys Arg Arg Leu Arg Arg Lys Ser Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Gly Leu Arg Trp Arg Arg Lys Arg Arg Lys Ser Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Gly Leu Arg Ile Arg Arg Leu Arg Arg Lys Ser Cys
```

```
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Gly Leu Arg Ile Arg Arg Leu Arg Arg His Arg Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 9

Gly Leu Arg Lys Arg Arg Leu Arg Arg His Ser Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 10

Gly Leu Arg Ile Arg Arg Leu Arg Arg His Ser Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 11

Lys Leu Arg Ile Arg Arg Leu Arg Arg His Ser Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 12

Gly Leu Arg Ile Arg Arg Leu Arg Arg His Ser Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 13

Gly Leu Arg Ile Arg Arg Leu Arg Ala Arg Ser Cys
1               5                   10
```

<210> SEQ ID NO 14
<211> LENGTH: 458
<212> TYPE: PRT
<213> ORGANISM: Artificial Sequence
<220> FEATURE:
<223> OTHER INFORMATION: Synthetic Peptide

<400> SEQUENCE: 14

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
                35                  40                  45

Asp Thr Phe Thr Asn Pro Glu Glu Gly Asp Leu Asn Pro Pro Pro Glu
            50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
                115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365
```

```
Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn
        450                 455

<210> SEQ ID NO 15
<211> LENGTH: 441
<212> TYPE: PRT
<213> ORGANISM: Artificial Sequence
<220> FEATURE:
<223> OTHER INFORMATION: Synthetic Peptide

<400> SEQUENCE: 15

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270
```

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg
        435                 440

<210> SEQ ID NO 16
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 16

Thr Gln Ile Asp Leu Ile Arg Lys Lys Met Lys Glu Ala Leu
1               5                   10

<210> SEQ ID NO 17
<211> LENGTH: 33
<212> TYPE: DNA
<213> ORGANISM: Artificial Sequence
<220> FEATURE:
<223> OTHER INFORMATION: Primer (GFP - forward primer)

<400> SEQUENCE: 17
tcgaaggtag gcatatggtg agcaagggcg agg                                    33

<210> SEQ ID NO 18
<211> LENGTH: 43
<212> TYPE: DNA
<213> ORGANISM: Artificial Sequence
<220> FEATURE:
<223> OTHER INFORMATION: Primer (GFP - reverse primer)

<400> SEQUENCE: 18
gcttgaattc ggatcctcac ttgtacagct cgtccatgcc gag                         43

<210> SEQ ID NO 19
<211> LENGTH: 33
<212> TYPE: DNA
<213> ORGANISM: Artificial Sequence
<220> FEATURE:
<223> OTHER INFORMATION: Primer (GFP-CDP1 - forward primer)

-continued

<400> SEQUENCE: 19
tcgaaggtag gcatatggtg agcaagggcg agg　　　　　　　　　　　　　　　33

<210> SEQ ID NO 20
<211> LENGTH: 70
<212> TYPE: DNA
<213> ORGANISM: Artificial Sequence
<220> FEATURE:
<223> OTHER INFORMATION: Primer (GFP-CDP1 - reverse primer)

<400> SEQUENCE: 20
gcttgaattc ggatcctcag caacggggtt tacgcagacg ggaacgtttc cccttgtaca　　60 gctcgtccat　　　　　　　　　　　　　　　　　　　　　　　　　　　　70

<210> SEQ ID NO 21
<211> LENGTH: 33
<212> TYPE: DNA
<213> ORGANISM: Artificial Sequence
<220> FEATURE:
<223> OTHER INFORMATION: Primer (GFP-CDP2 - forward primer)

<400> SEQUENCE: 21
tcgaaggtag gcatatggtg agcaagggcg agg　　　　　　　　　　　　　　　33

<210> SEQ ID NO 22
<211> LENGTH: 70
<212> TYPE: DNA
<213> ORGANISM: Artificial Sequence
<220> FEATURE:
<223> OTHER INFORMATION: Primer (GFP-CDP2 - reverse primer)

<400> SEQUENCE: 22
gcttgaattc ggatcctcag catttacgct tacgcaagcg ccagatgcgg cacttgtaca　　60 gctcgtccat　　　　　　　　　　　　　　　　　　　　　　　　　　　　70

<210> SEQ ID NO 23
<211> LENGTH: 33
<212> TYPE: DNA
<213> ORGANISM: Artificial Sequence
<220> FEATURE:
<223> OTHER INFORMATION: Primer (GFP-CDP3 - foward primer)

<400> SEQUENCE: 23
tcgaaggtag gcatatggtg agcaagggcg agg　　　　　　　　　　　　　　　33

<210> SEQ ID NO 24
<211> LENGTH: 74
<212> TYPE: DNA
<213> ORGANISM: Artificial Sequence
<220> FEATURE:
<223> OTHER INFORMATION: Primer (GFP-CDP3 - reverse primer)

<400> SEQUENCE: 24
gcttgaattc ggatcctcag gcaggagcgg cggcgcaaac gacgaatacg caacccttg　　60 tacagctcgt ccat　　　　　　　　　　　　　　　　　　　　　　　　74

<210> SEQ ID NO 25
<211> LENGTH: 33
<212> TYPE: DNA
<213> ORGANISM: Artificial Sequence
<220> FEATURE:
<223> OTHER INFORMATION: Primer (GFP-TAT - forward primer)

<400> SEQUENCE: 25

```
tcgaaggtag gcatatggtg agcaagggcg agg                                33
```

<210> SEQ ID NO 26
<211> LENGTH: 76
<212> TYPE: DNA
<213> ORGANISM: Artificial Sequence
<220> FEATURE:
<223> OTHER INFORMATION: Primer (GFP-TAT - reverse primer)

<400> SEQUENCE: 26

```
gcttgaattc ggatcctcat tgtggtggac ggcgacgctg gcgacgtttc ttgcgtccct   60
tgtacagctc gtccat                                                   76
```

<210> SEQ ID NO 27
<211> LENGTH: 33
<212> TYPE: DNA
<213> ORGANISM: Artificial Sequence
<220> FEATURE:
<223> OTHER INFORMATION: Primer (GFP-TD1 - forward primer)

<400> SEQUENCE: 27

```
tcgaaggtag gcatatggtg agcaagggcg agg                                33
```

<210> SEQ ID NO 28
<211> LENGTH: 76
<212> TYPE: DNA
<213> ORGANISM: Artificial Sequence
<220> FEATURE:
<223> OTHER INFORMATION: Primer (GFP-TD1 - reverse primer)

<400> SEQUENCE: 28

```
gcttgaattc ggatcctcaa cactgattca agaatttgtt aatgttaatc attgctttct   60
tgtacagctc gtccat                                                   76
```

CELL PENETRATING PEPTIDES AND USES THEREOF

CROSS REFERENCE TO PRIOR APPLICATIONS

This application is a National Stage Application of PCT International Patent Application No. PCT/KR2020/016357 filed on Nov. 19, 2020, under 35 U.S.C. § 371, which claims priority to Korean Patent Application Nos. KR10-2019-0161346 and KR10-2020-0099210 filed on Dec. 6, 2019 and Aug. 7, 2020, respectively, which are all hereby incorporated by reference in their entirety.

TECHNICAL FIELD

The present disclosure relates to novel cell penetrating peptides and their uses.

More specifically, the present disclosure relates to cosmetic composition comprising novel cell penetrating peptides, cell penetrating botulinum toxin recombinant proteins in which the cell-penetrating peptide and botulinum toxin are fused, polynucleotides encoding the cell penetrating botulinum toxin recombinant proteins, recombinant expression vector comprising the polynucleotides, and the cell penetrating botulinum toxin recombinant protein as active ingredients.

BACKGROUND

In general, botulinum toxin (BTX) is a toxin produced by *Clostridium botulinum*, a gram-positive anaerobic bacterium, and it has a mechanism that induces the relaxation and contraction of muscles by blocking exocytosis of acetylcholine by acting on the cholinergic nerve endings.

The botulinum toxin can be classified into seven neurotoxins (A-G types) by serotype, and the size of pure botulinum toxin is approximately 150 kDa, consisting of a heavy chain of 100 kDa and a light chain of 50 kDa.

The light chain of botulinum toxin is known to cleave some proteins in the SNARE complex, which is important for exocytosis in cholinergic nerve endings. For example, botulinum toxin type A, most widely used, cleaves SNAP-25 protein among SNARE complexes, and botulinum toxin type B cuts VAMP protein among SNARE complexes.

Meanwhile, the 100 kDa heavy chain is divided into two parts: a 50 kDa of receptor binding domain, which combines the entire toxin and the neuron, and a 50 kDa translocation domain, which pushes the botulinum toxin light chain out of the endosome when the botulinum toxin is internalized in nerve cells and stays in the endosome.

In general, when *Clostridium botulinum* produces botulinum toxin, it is produced as a complex of non-toxin proteins in addition to pure botulinum toxin protein. The size of the production can be up to approximately 900 kDa depending on the type of neurotoxin.

Botulinum toxin causes paralysis by blocking signals that cause the spasm and contraction of muscles. It has been used for cosmetic purposes to reduce skin wrinkles and therapeutic purposes by using these properties since it was approved by US FDA in 1989. For therapeutic purposes, it is used for neuromuscular diseases such as hyperhidrosis, migraine, strabismus, torticollis, or blepharospasm. For cosmetic purposes, it is used as an injection for removing wrinkles and frown wrinkles and treating a square jaw line. Dysphagia, voice change, dry mouth, and blurred vision have been reported side effects, but it is considered as a very safe medicine because there are no direct deaths due to botulinum toxin prescription yet. However, the application of it is restricted if a subject is hypersensitive to drugs, a subject has a musculoskeletal disorder, a subject is pregnant, or a subject is a nursing mother.

Currently, when botulinum toxin is used for cosmetic or therapeutic purposes, patients must be given an injection every 3-5 months to the affected site. When signal transmission between nerves and muscles is blocked by the botulinum toxin, a new nerve branch is generated to alleviate the nerve paralysis due to botulinum toxin. Thus, it requires regular treatment.

Moreover, when the injectable botulinum toxin is administered frequently, it may cause serious side effects due to bruises, allergies, wounds, and intravascular injections. Hence, there is a need to find other effective delivery means that can be convenient for patients.

Meanwhile, the skin, which is a bodily tissue that is always in contact with the external environment, plays an important role as a protective barrier to prevent body fluid leakage, infection, and moisture loss. It is composed of epidermis, dermis, and subcutaneous tissue.

The stratum corneum of the epidermis exists on the outermost part of the skin. It prevents drying of the skin by inhibiting the loss of moisture and electrolytes outside the skin and provides an environment that allows normal biochemical metabolism of the skin. The stratum corneum also plays important roles in protecting the human body from external physical damage and chemical substances and preventing bacteria, fungi, and viruses from invading the skin.

There are three absorption paths through the skin: absorption through the stratum corneum, absorption through the hair follicle and sebaceous gland, and absorption through the sweat gland. The delivery of active substances through the skin has several limitations due to the structural and physical characteristics of the skin. In particular, the stratum corneum of the skin has a dense structure in the outermost layer of the skin because of the natural death of keratinocytes, the major component cells of the skin and the pH of it is around 5 due to sweat and various lipid components. It is reported that the molecular weight must be 1,000 or less and it has to possess lipophilic properties to penetrate the stratum corneum barrier.

It is known that low-molecular synthetic compounds or natural compounds that are frequently used as cosmetic or medicinal ingredients can be easily delivered into cells. However, macromolecules such as proteins, peptides, and nucleic acids cannot penetrate the cell membrane, a double lipid membrane, due to their molecular weight and hydrophilic properties. It is known that low molecular weight substances have extremely low penetration efficiency and high molecular weight substances have even lower penetration efficiency due to the unique characteristics of the stratum corneum constituting the skin barrier.

Thus, it is essential to have a transporter that can deliver botulinum toxin through this skin barrier to transdermally deliver botulinum toxin. A cell penetrating peptide can be applied can be used as a method for amplifying the penetration efficiency of these small and macromolecules through the cell membrane.

Well-known cell penetrating peptides (CPPs) include HIV-Tat and antennapedia. They are mostly short-length peptides composed of less than 30 amino acids that are positively charged.

They are known to be able to deliver DNAs, RNAs, fats, carbohydrates, compounds, or viruses into cells, as well as proteins. It has been reported that they are receptor-independent, and they penetrate the cell membrane using various mechanisms such as endocytosis, phagocytosis, and direct penetration.

In fact, many publications have proposed the recombinant proteins comprising botulinum toxin and CPPs as a new medicine. These publications include Related Art Document 1, which is a review article introducing many transdermal delivery paths and claiming that transdermal delivery of botulinum toxin will be actually effective in treating neuromuscular diseases, and Related Art Document 2, which confirms skin permeability by recombining HIV-Tat, the most representative CPP, and botulinum toxin light chain.

However, since HIV-Tat, the most widely used peptide, is derived from a virus, a problem is raised in terms of safety. Thus, it was necessary to develop a novel CPP with better cell permeability than conventional CPPs for the development of botulinum toxin protein to be applied to the skin while considering the convenience of patients.

In response to these needs, we developed 13 new CPPs with higher cargo (e.g., compounds, peptides, and proteins) delivery efficiency than conventional CPPS by using the in silico method.

They were named Cargo Delivery Peptides (CDPs).

RELATED ART DOCUMENT

Non-Patent Document

Non-Patent Document 1: Current Drug Delivery. 2018. 15(10). 1375-1380
Non-Patent Document 2: Applied Microbial And Biotechnology. 2016. 100(6). 2785-2795

SUMMARY OF THE INVENTION

Challenge to be Solved

The Inventors developed CPPs that can deliver botulinum toxin more efficiently through cell permeation or skin permeation to solve the problems of the related art. The Inventors also aim to provide cosmetic compositions comprising novel cell penetrating peptides, cell penetrating botulinum toxin recombinant proteins in which the cell-penetrating peptide and botulinum toxin are fused, polynucleotides encoding the cell penetrating botulinum toxin recombinant proteins, recombinant expression vector comprising the polynucleotides, and the cell penetrating botulinum toxin recombinant protein as active ingredients by confirming that they can be applied in various fields in the cell penetrating botulinum toxin recombinant protein form and others by using them.

Means to Solve the Challenge

The present disclosure, to solve the above-mentioned challenge,

It is a peptide capable of mediating the transport of an active molecule into a cell, wherein the peptide provides CPPs consisting of one amino acid sequence selected from a group consisting of sequence number 1 to sequence number 13.

An exemplary embodiment of the present disclosure also provides CPPs, characterized in that the active molecule is at least one type selected from the group consisting of growth factors, enzymes, transcription factors, toxins, antigenic peptides, antibodies, antibody fragments, nucleic acids, coding nucleic acid sequences, mRNAs, antisense RNA molecules, microRNAs, siRNAs, carbohydrates, lipids, and glycolipids.

An exemplary embodiment of the present disclosure also provides botulinum toxin; and cell penetrating botulinum toxin recombinant proteins fused with CPPs.

An exemplary embodiment of the present disclosure also provides cell penetrating botulinum toxin recombinant proteins, characterized in that the botulinum toxin is one selected from the group consisting of serotypes A, B, C, D, E, F, and G.

An exemplary embodiment of the present disclosure also provides cell penetrating botulinum toxin recombinant proteins, characterized in that the CPP is fused to the carboxy terminal or amino terminal of the botulinum toxin light chain or all of them.

An exemplary embodiment of the present disclosure also provides cell penetrating botulinum toxin recombinant proteins, characterized in that the fusion is achieved by a peptide bond or a covalent bond.

An exemplary embodiment of the present disclosure, the cell penetrating botulinum toxin recombinant protein, also provides cell penetrating botulinum toxin recombinant proteins, characterized by sequential fusion of the botulinum toxin light chain peptide consisting of the amino acid sequence number 14 and number 15; translocation region peptides of botulinum toxin heavy chain consisting of the amino acid sequence number 16; and CPPs.

An exemplary embodiment of the present disclosure, the cell penetrating botulinum toxin recombinant protein, also provides cell penetrating botulinum toxin recombinant proteins, characterized in that it further includes a linker in any one or more among the gap between the CPP and the botulinum toxin light chain peptide, that between the botulinum toxin light chain peptide and the translocation region peptide of the botulinum toxin heavy chain, or that between the translocation region peptide of the botulinum toxin heavy chain and CPPs.

An exemplary embodiment of the present disclosure also provides polynucleotides encoding the cell penetrating botulinum toxin recombinant protein.

An exemplary embodiment of the present disclosure also provides recombinant expression vectors including the polynucleotide.

An exemplary embodiment of the present disclosure, the recombinant expression vector, also provides recombinant expression vectors characterized in that it includes at least one type of affinity label selected from the group consisting of His, FLAG, HAT, SBP, c-myc, chitin-binding domain, glutathione-S transferase, and maltose binding protein.

An exemplary embodiment of the present disclosure, the recombinant expression vector, also provides recombinant expression vectors characterized in that it includes at least one regulatory gene selected from the group consisting of cold shock protein A promoter, T7, Toc, BAD, and pRha.

An exemplary embodiment of the present disclosure also provides a cosmetic composition including the above-stated cell penetrating botulinum toxin recombinant protein as an active ingredient.

An exemplary embodiment of the present disclosure, the cosmetic composition, also provides cosmetic compositions, characterized by further including a skin emulsifier.

An exemplary embodiment of the present disclosure also provides cosmetic compositions, characterized in that the skin emulsifier is glyceryl monostearate or cetyl alcohol.

An exemplary embodiment of the present disclosure also provides cosmetic compositions, characterized in that the skin emulsifier is contained at least 0.5 w/w % based on the total weight of the composition.

An exemplary embodiment of the present disclosure, the cosmetic composition, also provides cosmetic compositions for improving or preventing skin wrinkles.

Effects of Invention

The CPP according to an exemplary embodiment of the present disclosure may be actively used as a topical agent for various disease treatment, aesthetic, or cosmetic purposes, especially for a cosmetic composition by securing better convenience as well as maximizing the intrinsic in vivo efficacy of the botulinum toxin through the cell penetrating recombinant proteins that combines the botulinum toxin and a CPP by making skin penetration and/or cell penetration for botulinum toxin more efficient.

BRIEF DESCRIPTION OF THE DRAWINGS

The accompanying drawings are only to explain the exemplary embodiment of the present disclosure in more detail for those skilled in the related art, and the technical idea of the present disclosure is not limited thereto.

FIG. 1 is a table comparing CDP 1 to CDP 13, novel CPPs derived from the exemplary embodiment 1 of the present disclosure to the conventional CPPs and predicted SVM scores.

FIG. 2 shows a diagram illustrating an exemplary protein expression vector according to the present disclosure.

FIG. 3 shows the results of electrophoresis performed to confirm the expression and purification of the GFP-Cargo Delivery Peptide recombinant protein in the Exemplary Embodiment 3 of the present disclosure. FIG. 3(a) shows the results of electrophoresis performed to confirm the expression and purification of CDP1 and CDP2 in the Exemplary Embodiment 3 of the present disclosure. FIG. 3(b) shows the results of electrophoresis performed to confirm the expression and purification of CDP3 in the Exemplary Embodiment 3 of the present disclosure. FIG. 3(c) shows the results of electrophoresis performed to confirm the expression and purification of TAT and TD1 in the Exemplary Embodiment 3 of the present disclosure. FIG. 3(d) shows the results of electrophoresis performed to confirm the expression and purification of GFP in the Exemplary Embodiment 3 of the present disclosure.

FIG. 4 is a diagram illustrating the results of confocal microscope observation regarding the human skin tissue permeability of CDP1, CDP2, and CDP3, GFP-Cargo Delivery Peptide recombinant proteins, in the Exemplary Embodiment 4 of the present disclosure. FIG. 4(a) is a diagram illustrating the results of confocal microscope observation regarding the human skin tissue permeability of CDP1, in the Exemplary Embodiment 4 of the present disclosure. FIG. 4(b) is a diagram illustrating the results of confocal microscope observation regarding the human skin tissue permeability of CDP2, in the Exemplary Embodiment 4 of the present disclosure. FIG. 4(c) is a diagram illustrating the results of confocal microscope observation regarding the human skin tissue permeability of CDP3, in the Exemplary Embodiment 4 of the present disclosure. FIG. 4(d) is a diagram illustrating the results of confocal microscope observation regarding the human skin tissue permeability of GFP, in the Exemplary Embodiment 4 of the present disclosure.

FIG. 5 is a diagram illustrating the results of confocal microscope observation comparing the human skin tissue permeability of CDP2, a GFP-Cargo Delivery Peptide recombinant protein, in the Exemplary Embodiment 4 of the present disclosure, and that of TD1, a conventional CPP. FIG. 5(a) is a diagram illustrating the results of confocal microscope observation comparing the human skin tissue permeability of CDP2, in the Exemplary Embodiment 4 of the present disclosure. FIG. 5(b) is a diagram illustrating the results of confocal microscope observation comparing the human skin tissue permeability of TD1, in the Exemplary Embodiment 4 of the present disclosure. FIG. 5(c) is a diagram illustrating the results of confocal microscope observation comparing the human skin tissue permeability of GFP, in the Exemplary Embodiment 4 of the present disclosure.

FIG. 6 is a diagram illustrating the results of confocal microscope observation comparing the human skin tissue permeability of CDP1, a GFP-Cargo Delivery Peptide recombinant protein, in the Exemplary Embodiment 4 of the present disclosure, and that of HIV-Tat, a conventional CPP. FIG. 6(a) is a diagram illustrating the results of confocal microscope observation the human skin tissue permeability of CDP1, a GFP-Cargo Delivery Peptide recombinant protein, in the Exemplary Embodiment 4 of the present disclosure. FIG. 6(b) is a diagram illustrating the results of confocal microscope observation the human skin tissue permeability of HIV-Tat, a conventional CPP, in the Exemplary Embodiment 4 of the present disclosure.

FIG. 7 is a diagram illustrating the results of electrophoresis performed on a 10% SDS-PAGE gel to test whether the recombinant protein was appropriately purified in the Exemplary Embodiment 6 of the present disclosure. FIG. 7(a) is a diagram illustrating the results of electrophoresis performed on a 10% SDS-PAGE gel to test whether the recombinant protein was appropriately purified of CDP1 in the Exemplary Embodiment 6 of the present disclosure. FIG. 7(b) is a diagram illustrating the results of electrophoresis performed on a 10% SDS-PAGE gel to test whether the recombinant protein was appropriately purified of CDP3 in the Exemplary Embodiment 6 of the present disclosure. FIG. 7(c) is a diagram illustrating the results of electrophoresis performed on a 10% SDS-PAGE gel to test whether the recombinant protein was appropriately purified of TAT in the Exemplary Embodiment 6 of the present disclosure. FIG. 7(d) is a diagram illustrating the results of electrophoresis performed on a 10% SDS-PAGE gel to test whether the recombinant protein was appropriately purified of TD1 in the Exemplary Embodiment 6 of the present disclosure.

FIG. 8 depicts the result of FITC fluorescence observation in the exemplary embodiment 7 of the present disclosure. FIG. 8(a) depicts the result of FITC fluorescence observation of BTA-CDP1 in the exemplary embodiment 7 of the present disclosure. FIG. 8(b) depicts the result of FITC fluorescence observation of BTA-CDP3 in the exemplary embodiment 7 of the present disclosure. FIG. 8(c) depicts the result of FITC fluorescence observation of BTA-TAT in the exemplary embodiment 7 of the present disclosure. FIG. 8(d) depicts the result of FITC fluorescence observation of BTA-TD1 in the exemplary embodiment 7 of the present disclosure. FIG. 8(e) depicts the result of FITC fluorescence observation of PBS in the exemplary embodiment 7 of the present disclosure.

FIG. 9 is a diagram showing the results of FITC fluorescence observation in the exemplary embodiment 8 of the present disclosure. FIG. 9(a) is a diagram showing the results of FITC fluorescence observation of CDP1-BTA in the exemplary embodiment 8 of the present disclosure.

FIG. 9(b) is a diagram showing the results of FITC fluorescence observation of CDP3-BTA in the exemplary embodiment 8 of the present disclosure. FIG. 9(c) is a diagram showing the results of FITC fluorescence observation of CDP1-BTA with added emulsifier in the exemplary embodiment 8 of the present disclosure.

FIGS. 10 and 11 illustrate the absorbance and WST-1 assay results (cellular viability) measured in the exemplary embodiment 9 of the present disclosure.

FIGS. 12 and 13 illustrate the results of fluorescence measurement measured in the exemplary embodiment 10 of the present disclosure.

BEST MODE FOR CARRYING OUT THE INVENTION

Hereinafter, the present disclosure explains a recombinant expression vector including novel cell penetrating peptides, cell penetrating botulinum toxin recombinant proteins in which the CPP and botulinum toxin are fused, polynucleotides encoding the cell penetrating botulinum toxin recombinant protein, and the polynucleotide according to an exemplary embodiment of the present disclosure, and cosmetic composition including the cell penetrating botulinum toxin recombinant protein as an active ingredient in detail. However, the scope of a right of the recombinant expression vector including novel cell penetrating peptides, cell penetrating botulinum toxin recombinant proteins in which the CPP and botulinum toxin are fused, polynucleotides encoding the cell penetrating botulinum toxin recombinant protein, and the polynucleotide, and cosmetic composition including the cell penetrating botulinum toxin recombinant protein as an active ingredient is not limited by the following description.

Besides, throughout the specification, when a part "includes" a certain component, it means that other components may be further included rather than excluding other components unless otherwise specified.

The terminology "botulinum toxin" used herein also includes variants and fusion proteins produced or engineered by bacteria or by recombinant technology and it is used to include all known types of botulinum toxins, regardless of whether it may subsequently be found.

The present disclosure is regarding a novel peptide.

More specifically, the present disclosure relates to a novel cell penetrating peptide (CPP).

The CPP preferably does not have an enzyme or therapeutic biological activity defined by itself, but it works as a carrier that enables intracellular transport through the cell membrane. It can be attached to the N-terminal, C-terminus, or both terminals of a cargo to be delivered into the cell, and it can be attached in the forward or reverse direction at each terminal. The peptide according to the present disclosure will preferably be applied as a monomer, but it is not limited thereto, and it may be used in the form of a dimer or a polymer.

The peptide of the present disclosure may be a peptide capable of mediating the transport of an active molecule into a cell.

In this case, the active molecule may be one or more selected from a group that consists of growth factors, enzymes, transcription factors, toxins, antigenic peptides, antibodies, antibody fragments, nucleic acids, coding nucleic acid sequences, mRNAs, antisense RNA molecules, microRNAs, siRNAs, carbohydrates, lipids, and glycolipids, but is not particularly limited thereto.

The CPP according to the present disclosure may consist of one type of amino acid sequence selected from the group composed of sequence number 1 to sequence number 13.

When the CPP according to the present disclosure consists of one type of amino acid sequence selected from the group consisting of sequence number 1 to sequence number 13 as described above, it can maximize the in vivo efficacy of botulinum toxin by making the skin penetration or cell penetration of botulinum toxin more efficient through chemical bonding with botulinum toxin as described below and it may be used for various purposes.

The present disclosure also relates to a recombinant protein.

More specifically, the present disclosure relates to a cell penetrating botulinum toxin recombinant protein.

The terminology "cell penetrating botulinum toxin recombinant protein" used herein includes the CPP and botulinum toxin, and may refer to an assembly formed by chemical bonding such as a peptide bond or a covalent bond of them. That is, the cell penetrating botulinum toxin recombinant protein can deliver the botulinum toxin into the cell with high efficiency by giving cell permeability by fusing a specific cell penetrating peptide with botulinum toxin, which is a macromolecule that is difficult to transport into the cell. In this case, the CCP may be fused to the carboxy terminal of the botulinum toxin light chain, the amino terminal of it, or both.

As described above, the cell penetrating botulinum toxin recombinant protein according to the present disclosure is not particularly limited. For example, it may have a structure or a form of fusing botulinum toxin and the CPP.

The botulinum toxin light chain may be one type selected from the group consisting of serotypes A, B, C, D, E, F, and G. In the present disclosure, the botulinum toxin light chain may include alternatively botulinum toxin derivatives, which is a compound that has botulinum toxin activity but arbitrarily having one or more modifications on a portion or sequence. For example, they may be a modified form in a way that enhances properties or reduces side effects while maintaining the endopeptidase activity of the light chain by applying methods such as deletion, modification, replacement, or chimeric fusion on the amino acid sequence, in contrast to the seven serotypes of botulinum toxin light chain proteins. Alternatively, it may use a botulinum toxin light chain prepared by recombinant or chemical synthesis or a portion of a botulinum toxin light chain.

In an exemplary embodiment, the botulinum toxin light chain may consist of the amino acid sequence number 14 or sequence number 15.

In an exemplary embodiment, the cell penetrating botulinum toxin recombinant protein according to the present disclosure includes a botulinum toxin light chain peptide consisting of the amino acid sequence number 14 or sequence number 15; the translocation region peptide of the botulinum toxin heavy chain consisting of the amino acid sequence number 16; and a structure or a form in which the CPPs are sequentially fused.

When the cell penetrating botulinum toxin recombinant protein according to the present disclosure has the above-described structure or form, it can be actively used as a topical agent for various disease treatment, aesthetic, or cosmetic purposes by making the skin penetration and/or cell penetration of botulinum toxin more efficient, maximizing the in vivo intrinsic efficacy of the botulinum toxin, and securing better convenience at the same time.

In an exemplary embodiment, the cell penetrating botulinum toxin recombinant protein according to the present disclosure may additionally include a linker in any one or more among the gap between the CPP and the botulinum toxin light chain peptide, that between the botulinum toxin light chain peptide and the translocation region peptide of the botulinum toxin heavy chain, or that between the translocation region peptide of the botulinum toxin heavy chain and CPPs.

The type of the linker, although not particularly limited, may consist of various amino acid sequences. For example, it may be a form of combining multiple glycine amino acids, or may be a form bound to a specific amino acid sequence. However, it is preferable that it is a form conjugated to a specific amino acid sequence.

The present disclosure also relates to a polynucleotide that encodes the cell penetrating botulinum toxin recombinant protein and a recombinant expression vector including the polynucleotide.

The terminology "recombinant expression vector" used herein is a vector that is capable of expressing a protein of interest or an RNA of interest in a suitable host cell, and it may refer to a gene construct including essential regulatory elements operably linked to express a gene insert.

The terminology "operably linked" may also mean that a nucleic acid expression regulator sequence and a nucleic acid sequence encoding a protein of interest or an RNA of interest are functionally linked to perform a general function. For example, the nucleic acid sequence coding a promotor, a protein, or an RNA is operably linked to affect the expression of the encoding nucleic acid sequence. Operably linked with the recombinant expression vector can be prepared using the gene recombination technique well known in the related art, and enzymes generally known in the related art can be used for site-specific DNA cleavage and ligation.

In an exemplary embodiment, the expression vector includes a plasmid vector, a cosmid vector, a bacteriophage vector, a viral vector, and others, but it is not particularly limited thereto. Appropriate expression vectors can be prepared in various ways according to the purpose, including a signal sequence or a leader sequence for membrane targeting or secretion besides expression regulatory sequences such as promoters, operators, initiation codons, termination codons, polyadenylation signals, and enhancers. The promoter of the expression vector may be constitutive or inducible. Besides, the expression vector may include a selection marker for selecting a host cell containing the vector, and it may include a replication origin when it is a replicable expression vector.

The recombinant expression vector according to the present disclosure may also contain at least one type of affinity label selected from the group consisting of His, FLAG, HAT, SBP, c-myc, chitin-binding domain, glutathione-S transferase, and maltose binding protein.

The recombinant expression vector of the present disclosure may also contain at least one regulatory gene type selected from the group consisting of cold shock protein A promoter, T7, Toc, BAD, and pRha. In the present disclosure, it is preferable to use a regulatory gene expressed in a specific condition, and preferably, a cold shock protein A promoter may be used because, as the regulatory gene, the target protein is in the form of a toxin more than the general regulatory gene.

When the recombinant expression vector according to the present disclosure contains the above-described regulatory gene, it is possible to maximize the yield efficiency of an active protein by obtaining a larger amount of a target soluble protein. For example, when the recombinant expression vector according to the present disclosure includes a cold shock protein A promoter as a regulatory gene, it is possible to obtain the target protein with high yield and purity because it can suppress the expression of other cellular proteins at the same temperature. whereas the target protein can be expressed even at about 15° C. In this case, it is also possible to obtain activated proteins with a higher yield, since the solubility of the target protein increases.

The present disclosure also relates to a cosmetic composition.

More specifically, the present disclosure is regarding a cosmetic composition including the above-described cell penetrating botulinum toxin recombinant protein as an active ingredient.

The cosmetic composition of the present disclosure may be prepared in any formulation conventionally prepared in the related art. For example, it can be formulated as a solution, suspension, emulsion, paste, gel, cream, lotion, powder, soap, surfactant-containing cleansing, oil, powder foundation, emulsion foundation, and wax foundation, and others, but it is not limited thereto. More specifically, it may be prepared in the form of a skin, a nutritional toner, a nutritional cream, a massage cream, an essence, an eye cream, a cleansing cream, a cleansing foam, a cleansing water, a pack, or a powder.

The cosmetically effective carrier contained in the cosmetic composition of the present disclosure may be a carrier commonly used in the related art according to the formulation. When the formulation of the present disclosure is paste, cream, or gel, animal oil, vegetable oil, wax, paraffin, starch, tragacanth, cellulose derivative, polyethylene glycol, silicone, bentonite, silica, talc, or zinc oxide may be used as a carrier ingredient.

When the formulation of the cosmetic composition of the present disclosure is a solution or an emulsion, a solvent, a solubilizer, or an emulsifier may be used as a carrier ingredient. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan may be used.

When the formulation of the present invention is a suspension, a liquid diluent such as water, ethanol, or propylene glycol, a suspending agent such as an ethoxylated isostearyl alcohol, a polyoxyethylene sorbitol ester, and a polyoxyethylene sorbitan ester, and microcrystalline cellulose, aluminum metahydroxide, bentonite, agar, or tragacanth can be used.

When the formulation of the present disclosure is a surfactant containing cleansing, aliphatic alcohol sulfate, aliphatic alcohol ether sulfate, sulfosuccinetic acid monoester, isethionate, imidazolinium derivative, methyltaurate, sarcosinate, fatty acid amide ether sulfates, alkylamidobetaines, fatty alcohols, fatty acid glycerides, fatty acid diethanolamides, vegetable oils, lanolin derivatives, ethoxylated glycerol fatty acid esters, and others can be used as a carrier ingredient.

Ingredients included in the cosmetic composition of the present disclosure may include ingredients commonly used for cosmetic compositions besides active ingredients and carrier ingredients. For example, it may include moisturizers, antioxidants, air freshener, fillers, viscosity-increasing agents, dyes, colorings, surfactants, natural or synthetic oils, preservatives, penetrants, hydrating agents, antifungal agents, emulsifier solvents, softeners, deodorants, waxes, and others. It may include other ingredients commonly used in such products including selectively plant extracts, conditioning agents, pigmentation or whitening agents, sunscreens, humectants, vitamins, derivatives, and others.

In an exemplary embodiment, the cosmetic composition according to the present disclosure preferably further includes a skin emulsifier.

The terminology "skin emulsifier" used herein may refer to an ingredient that affects skin penetration among emulsifiers. In the present disclosure, it enhances the skin penetration and cell penetration of recombinant proteins. Although it can use one or more selected from the group consisting of lecithin, lauryl pyrrolidone, glyceryl monostearate, glycerol monooleate, glycerol monolaurate, propylene glycol monolaurate, polyoxyethylene sorbitan monooleate, polyoxyethylene sorbitan monostearate, polyoxyethylene sorbitan monolaurate, sorbitan monooleate, sorbitan monostearate, sorbitan monolaurate, and cetyl alcohol, glyceryl monostearate or cetyl alcohol is preferred.

In an exemplary embodiment, the skin emulsifier may be contained 0.5 w/w % or more based on the total weight of the composition. When transdermal penetration enhancer is included within the weight range, the cosmetic composition according to the present disclosure may maximize skin penetration.

The cosmetic composition according to the present disclosure may further include a sugar-alcohol that stabilizes the ingredients contained therein, and the sugar-alcohol may be mannitol, erythritol, xylitol, sorbitol, and others, but is not particularly limited thereto.

The cosmetic composition of the present disclosure also relates to a cosmetic composition for improving or preventing skin wrinkles.

The cosmetic composition of the present disclosure, as described above, can improve or prevent skin wrinkles when it is administrated locally because it includes the cell penetrating botulinum toxin recombinant protein as an active ingredient.

The terminology "local administration" used herein means directly administering a drug on, into, or near an animal body that requires a biological effect of the drug. Local administration excludes systemic routes such as intravenous or oral administration. Topical administration refers to applying a pharmaceutical agent on the skin of a person. That is, the "putting on the skin" type is also included as a form of the local administrations. The composition of the present disclosure is preferably administered by "applying it on" the skin transdermally for the above dermatologically and cosmetically desired effects.

Hereinafter, the present disclosure will be described in more detail using specific exemplary embodiments. However, these exemplary embodiments are to explain the present disclosure using examples only, and the scope of the present disclosure is not limited to these exemplary embodiments.

[Exemplary Embodiment 1] Preparation of a Novel CPP

Novel skin penetrating and cell penetrating peptides that can deliver the botulinum toxin light chain transdermally have been developed.

First, the structure and function of the botulinum toxin heavy and light chains were analyzed, and it was confirmed that it shows the most optimal cell permeability when the length of amino acids is between 11 and 15 due to the positive charge and structure of CCPs. In particular, considering that arginine has the best cell permeability, final 13 peptide types (amino acid sequence 1 to 13) according to the amino acid sequence of the protein by deriving proteins that are expected to have excellent cell permeability by checking the changes in cell permeability when each 11 and 12 arginine amino acid sequences are replaced with other amino acids.

The predicted cell permeability scores of the novel CPP CDPs 1 to 13 derived from the present disclosure using a database program that predicts cell permeability based on this were compared with those of the conventional CPPs, and it is shown in FIG. 1.

[Exemplary Embodiment 2] Preparation of Recombinant Expression Vector for the Production of GFP-Cargo Delivery Peptide Recombinant Protein GFP-CDP1, GFP-CDP2, and GFP-CDP3 recombinant proteins were produced as a test group by binding them with green fluorescent protein (GFP) to evaluate the cell permeability with CDP1, CDP2 and CDP3, CPPs, developed by the company. Trans-activator of transcription (TAT), known as a cell penetrating protein, GFP-TAT, a recombinant protein of GFP, translocation domain 1 (TD1) called a CPP in the domestic patent (10-1882461), and GFP-TD1, a recombinant protein of GFP were prepared and used as a control group. GFP was also used as a negative control group.

The used GFP was obtained from the pCMV-GFP (#11153) of Addgene, and a CPP was attached behind GFP using a poly chain reaction (PCR) through the prepared primer. The sequence information of each primer is shown in [Table 1].

TABLE 1

| | | |
|---|---|---|
| GFP | Forward primer | TCGAAGGTAGGCATATGGTGAGCAAGGGCGAGG (SEQ ID NO: 17) |
| | Reverse primer | GCTTGAATTCGGATCCTCACTTGTACAGCTCGTCCA TGCCGAG (SEQ ID NO: 18) |
| GFP-CDP1 | Forward primer | TCGAAGGTAGGCATATGGTGAGCAAGGGCGAGG (SEQ ID NO: 19) |
| | Reverse primer | GCTTGAATTCGGATCCTCAGCAACGGGGTTTACGCA GACGGGAACGTTTCCCCTTGTACAGCTCGTCCAT (SEQ ID NO: 20) |
| GFP-CDP2 | Forward primer | TCGAAGGTAGGCATATGGTGAGCAAGGGCGAGG (SEQ ID NO: 21) |
| | Reverse primer | GCTTGAATTCGGATCCTCAGCATTTACGCTTACGCA AGCGCCAGATGCGGCACTTGTACAGCTCGTCCAT (SEQ ID NO: 22) |
| GFP-CDP3 | Forward primer | TCGAAGGTAGGCATATGGTGAGCAAGGGCGAGG (SEQ ID NO: 23) |
| | Reverse primer | GCTTGAATTCGGATCCTCAGGCAGGAGCGGCGGCG CAAACGACGAATACGCAACCCCTTGTACAGCTCGT CCAT (SEQ ID NO: 24) |
| GFP-TAT | Forward primer | TCGAAGGTAGGCATATGGTGAGCAAGGGCGAGG (SEQ ID NO: 25) |
| | Reverse primer | GCTTGAATTCGGATCCTCATTGTGGTGGACGGCGAC GCTGGCGACGTTTCTTGCGTCCCTTGTACAGCTCGT CCAT (SEQ ID NO: 26) |
| GFP-TD1 | Forward primer | TCGAAGGTAGGCATATGGTGAGCAAGGGCGAGG (SEQ ID NO: 27) |
| | Reverse primer | GCTTGAATTCGGATCCTCAACACTGATTCAAGAATT TGTTAATGTTAATCATTGCTTTCTTGTACAGCTCGT CCAT (SEQ ID NO: 28) |

The PCR started with a final volume of 50 μl with μl of pCMV-GFP vector as a template, 0.5 μl of each 100 pmole primer, 0.5 μl of polymerase, 5 μl of 2.5 mM dNTP, and 5× buffer. The reaction condition was denaturing at 95° C. for 5 minutes, and then 25 repetitions of 30 seconds at 95° C., 30 seconds at 56° C., and 30 seconds at 72° C., and final amplification was performed at 72° C. for 5 minutes. After confirming this PCR product with agarose gel electrophoresis, it was prepared by cleaving it into Nde I and BamH I. The expression vector pCold I (TaKaRa #3360) with histidine-tag, lac operator, and cold shock protein A (cspA) promoter was prepared by cleaving Nde I and BamH I from multi cloning sites (MCS), and this was also confirmed by agarose gel electrophoresis. An expression vector was prepared by treating the insert and vector for 150 seconds at RT and ligating for 10 minutes on ice. This was transformed into E. coli top 10 cells to prepare a final recombinant protein expression vector. This was done by requesting to Cosmo Genetech.

[Exemplary Embodiment 3] Expression and Purification of GFP-Cargo Delivery Peptide Recombinant Protein A genetically modified organism was prepared by transforming a plasmid expressing the recombinant protein by applying the heat shock (42° C., 90 seconds) method to E. coli BL21 (TaKaRa #9126). The transformed strain was first cultured for about 18-22 hours at 37° C. in an LB medium containing 10 μl of ampicillin. As a secondary culture, 1 μl of primary cultured cells and 100 μl of ampicillin were added to 100 μl of LB medium and cultured at 37° C. until the OD 600 value of the cells reached 0.6-0.8.

The expression of the recombinant protein was induced while adding 0.5 mM IPTG (isopropyl β-d-1-thiogalactopyranoside), and it was cultivated for about 19 hours at 15° C. and 200 rpm. The cells were collected by centrifugation, and the cells were pulverized using a lysis buffer (xTractor buffer) provided by the Capturem™ His-Tagged Purification Maxiprep Kit (TaKaRa #635713) and a homogenizer. Then, it was centrifuged at 10,000 rpm and 4° C. for 20 minutes, and the supernatant was separated.

The purification process of the recombinant protein was to purify the supernatant using the Capturem™ His-Tagged Purification Maxiprep Kit. Afterward, the protein was put into a cellulose membrane and then it was dialyzed using 1 L phosphate buffer.

Electrophoresis was performed on a 10% SDSPAGE gel to test whether the recombinant protein was properly purified.

The results of the electrophoresis are shown in FIG. 3. In FIG. 3, M stands for "BIO_RAD standard (#161-0377)", UI stands for "Uninduced", I stands for "Induced", HS stands for "cell harvest & supernatant", Ly stands for "Lysate", P stands for "pellet", FT stands for "Flow Through", W stands for "Column wash", and E stands for "Elution".

As shown in FIG. 3, it was confirmed that the recombinant protein was well purified according to the above protocol considering that a high concentration of the recombinant protein was observed after elution on the SDS-PAGE gel.

[Exemplary Embodiment 4] Human Skin Tissue Permeability of GFP-Cargo Delivery Peptide Recombinant Protein The purified GFP-cell penetrating peptide recombinant protein 20-30 μg was spread on the donated real human skin (HuSKIN™, HansBiomed Corp) at 4° C. for about 24 hours. The tissue was fixed at 4° C. for 24 hours with 4% paraformaldehyde after 24 hours, and it was dehydrated using 4.5% sucrose, 15% sucrose, and 30% sucrose.

The tissue that had undergone the dehydration process was prepared as cryosection (20 m) using a Microm freezing microtome by requesting to the Korea Pathology Support. Afterward, GFP fluorescence was observed using a confocal microscopy after placing it on a slide.

Observation results are shown in FIGS. 4 to 6, respectively.

As shown in FIGS. 4 to 6, it was confirmed that the recombinant protein according to the present disclosure has a higher cell permeability than TAT and TD1 set as controls and GFP, a negative control.

[Exemplary Embodiment 5] Preparation of Recombinant Expression Vector for Producing Botulinum Toxin-Cargo Delivery Peptide Recombinant Protein BTA-CDP1, BTA-CDP3, and BTB-CDP3 recombinant proteins were prepared as test groups by combining a botulinum toxin light chain A type (BTLcA) and a botulinum toxin light chain B type (BTLcB) with a portion of a heavy chain to examine the botulinum toxin delivery efficacy of CDP1, CDP2, and CDP3, CPPs developed by the company. Trans-activator of transcription (TAT), known as a cell penetrating protein, BTA-TAT, a recombinant protein of botulinum toxin, and BTA-TD1, a recombinant protein of translocation domain 1 (TD1) called a CPP in the domestic patent (10-1882461) and botulinum toxin were prepared respectively and used as control groups.

First, the A type and B type light chain portion of botulinum toxin was prepared by synthesizing genes. A recombinant expression vector was prepared by attaching a CPP to the synthesized gene's C-terminal through PCR, ligating to pColdI vector by cleaving with NdeI/BamHI, and then transforming to TOP10 cell. This was conducted by requesting it to Cosmo Genetech.

[Exemplary Embodiment 6] Expression and Purification of Botulinum Toxin-Cargo Delivery Peptide Recombination Protein A genetically modified organism was prepared by transforming a plasmid expressing the recombinant protein by applying the heat shock (42° C., 90 seconds) method to E. coli BL21 (TaKaRa #9126). The transformed strain was primarily cultured for about 18-22 hours at 37° C. in an LB medium containing 10 μl of ampicillin. As a secondary culture, 1 μl of primary cultured cells and 100 μl of ampicillin were added to 100 μl of LB medium and cultured at 37° C. until the OD 600 value of the cells reached 0.6-0.8.

The expression of the recombinant protein was induced while adding 0.5 mM IPTG (isopropyl β-d-1-thiogalactopyranoside), and it was cultivated for about 19 hours at 15° C. and 200 rpm. The cells were collected by centrifugation, and the cells were pulverized using a lysis buffer (xTractor buffer) provided by the Capturem™ His-Tagged Purification Maxiprep Kit (TaKaRa #635713) and a homogenizer. Then, it was centrifuged at 10,000 rpm and 4° C. for 20 minutes, and the supernatant was separated.

The purification process of the recombinant protein was to purify the supernatant using a HisTrap FF (GE Healthcare) column. Afterward, the protein was put into a cellulose membrane and then it was dialyzed using 1 L phosphate buffer.

Electrophoresis was also performed on a 10% SDS-PAGE gel to test whether the recombinant protein was properly purified.

The results of the electrophoresis are presented in FIG. 7.

In FIG. 7, it was confirmed that the recombinant protein was well purified according to the above protocol considering that a high concentration of the recombinant protein was observed after elution on the SDS-PAGE gel.

[Exemplary Embodiment 7] Human Skin Tissue Permeability of Botulinum Toxin-Cargo Delivery Peptide Recombinant Protein The process of labeling FITC on the purified botulinum toxin-cargo delivery peptide recombinant protein was conducted using a Fluoro Tag FITC conjugation kit (Sigma-Aldrich). The recombinant protein was dissolved in 0.1M Sodium Carbonate-Bicarbonate Buffer pH 9.0, and FITC isomer was slowly added thereto. Afterward, it was stirred at 37° C. for 1 hour. The recombinant protein to which FITC was attached was purified using a NAP-5 column (GE Healthcare).

3 µg of recombinant protein fluorescently labeled with FITC was spread on the donated real human skin (HuSKIN™, HansBiomed Corp) at 4° C. for about 30 minutes. The tissue was fixed at 4° C. for 24 hours with 4% paraformaldehyde after 30 minutes, and it was dehydrated using 4.5% sucrose, 15% sucrose, and 30% sucrose.

The tissue that had undergone the dehydration process was prepared as cryosection (20 m) using a Microm freezing microtome by requesting to the Korea Pathology Support. Afterward, FITC fluorescence was observed using a confocal microscopy after placing it on a slide.

The results of the FITC fluorescence observation are shown in FIG. 8.

As shown in FIG. 8, it was confirmed that the botulinum toxin-cargo delivery peptide 1 recombinant protein (BTA-CDP1) of the company had the highest cell permeability compared to the control groups (BTA-TAT and BTA-TD1) and the negative control group (PBS).

[Exemplary Embodiment 8] Skin Penetration Test of a Composition Containing a Botulinum Toxin-Cargo Delivery Peptide Recombinant Protein and a Transdermal Penetration Enhancer A composition was prepared by mixing 3 µg of the recombinant protein fluorescently labeled with FITC prepared in the Exemplary Embodiment 7 using glycerol stearate (GMS), cetyl alcohol, which are transdermal penetration enhancers, and purified water.

The composition was spread on the donated real human skin (HuSKIN™, HansBiomed Corp) at 4° C. for about 30 minutes. The tissue was fixed at 4° C. for 24 hours with 4% paraformaldehyde after 30 minutes, and it was dehydrated using 4.5% sucrose, 15% sucrose, and 30% sucrose.

The tissue that had undergone the dehydration process was prepared as cryosection (20 m) using a Microm freezing microtome by requesting to the Korea Pathology Support. Afterward, FITC fluorescence was observed using a confocal microscopy after placing it on a slide.

The results of FITC fluorescence observation are shown in FIG. 9.

As shown in FIG. 9, when the botulinum toxin-cargo delivery peptide recombinant protein (BTA-CDP1) was used with a transdermal penetration enhancer, higher cell permeability could be confirmed.

[Exemplary Embodiment 9] Cytotoxicity Test of Botulinum Toxin-Cargo Delivery Peptide Recombinant Protein A WST-1 assay, measuring cell viability, was performed to evaluate the toxicity of the recombinant protein BT-CDP to skin cells. Human dermal fibroblasts were first cultured in a 96 well plate until it became at $5 \times 10^3$/well, and then it was treated with 5 to 80 µg of recombinant protein and reacted for 24 hours. After the reaction, 10 µl of Cell Proliferation Reagent WST-1 (Sigma-aldrich) was added to each and reacted for an additional 4 hours. Thereafter, absorbance was measured between 420 and 480 nm using an ELISA reader. In this case, a botulinum toxin protein not bound to a CPP was used as a control group, and the results of absorbance measurement are shown in FIGS. 10 and 11.

As shown in FIGS. 10 and 11, the results of the WST-1 assay confirmed that the recombinant protein (5-80 µg) did not show toxicity, compared to TCPS.

[Exemplary Embodiment 10] SNAP-25 Cleavage Assay of Botulinum Toxin-Cargo Delivery Peptide Recombinant Protein A cleavage assay was performed to measure the activity (proteolytic ability) of the botulinum toxin contained in the recombinant protein BTA-CDP. Among soluble N-ethylmaleimide-sensitive factor activating protein receptor (SNARE) proteins that botulinum toxin degrades in the body, SNAPtide® (Cat. #521, List Biological Laboratories, Inc., Campbell, CA), made by synthesizing a part of the original sequence of the SNAP-25 protein decomposed by botulinum toxin A type, and attaching a fluorescent substance was used. The proteolytic ability of botulinum toxin can be quantitatively measured by using the fluorescence resonance energy transfer (FRET) effect, which shows little fluorescence until it is decomposed by botulinum toxin and then emits light as the distance between the fluorescent substances on both ends increases when it is hydrolyzed by the toxin. First, samples were prepared in HEPES (4-(2-hydroxyethyl)-1-piperazineethanesulfonic acid) buffer at a concentration of 100 µg/ml by measuring the concentration of the recombinant protein. 10M stock solution was prepared by dissolving the purchased SNAPtide® in DMSO. A 96 well clear bottom black plate (Corning®, CLS3603) was prepared for the reaction, the prepared recombinant protein was added to the well at a concentration of 10 µg/ml, and SNAPtide® was added to a well at a concentration of 5 µM.

After mixing them, the reaction was initiated. The reaction was conducted at 37° C., and the fluorescence measurement was performed for about 2 hours at a wavelength of excitation 490 nm/emission 523 nm/cutoff 495 nm.

The recorded results are shown in FIGS. 12 and 13.

As shown in FIGS. 12 and 13, the results of the SNAP-25 cleavage assay revealed that the botulinum toxin-cargo delivery peptide recombinant protein activated botulinum toxin.

The results of Exemplary Embodiments 5 to 10 showed that the botulinum toxin-cell penetrating peptide recombinant protein according to the present disclosure made the skin penetration and/or cell penetration efficient to maximize the in vivo intrinsic efficacy of the botulinum toxin and secure convenience. Hence, it can be actively used as a topical agent for various disease treatment, aesthetic or cosmetic purposes, especially for a cosmetic composition.

The description of the present application is for exemplary embodiments, it is to be understood that the disclosure is intended to cover various modifications and equivalent arrangements included within the spirit and scope of the appended claims. Thus, it should be understood that the embodiments described above are illustrative and are not limited to the disclosed embodiments. For example, each component described as a single type may be implemented in a distributed manner, and similarly, components described as being distributed may also be implemented in a combined form.

The scope of the present application is indicated by the claims to be described later rather than the above-stated description. All changes or modified forms derived from the meaning, scope, and equivalent concepts of the claims should be interpreted as being included in the scope.

```
Sequence List Free Text
<Sequence List 1>
                                              (SEQ ID NO: 1)
GKRSRLRKPR C <Sequence List2>
                                              (SEQ ID NO: 2)
CRIWRLRKRK C <Sequence List3>
                                              (SEQ ID NO: 3)
GLRIRRLRRR SC <Sequence List4>
                                              (SEQ ID NO: 4)
GLRRRRKRKR SC <Sequence List5>
                                              (SEQ ID NO: 5)
GLRKRRLRRK SC <Sequence List6>
                                              (SEQ ID NO: 6)
GLRWRRKRRK SC <Sequence List7>
                                              (SEQ ID NO: 7)
GLRIRRLRRK SC <Sequence List8>
                                              (SEQ ID NO: 8)
GLRIRRLRRH RC <Sequence List9>
                                              (SEQ ID NO: 9)
GLRKRRLRRH SC <Sequence List10>
                                              (SEQ ID NO: 10)
GLRIRRLRRH SK <Sequence List11>
                                              (SEQ ID NO: 11)
KLRIRRLRRH SC <Sequence List12>
                                              (SEQ ID NO: 12)
GLRIRRLRRH SC <Sequence List13>
                                              (SEQ ID NO: 13)
GLRIRRLRAR SC <Sequence List14>
                                              (SEQ ID NO: 14)
MPFVNKQFNY KDPVNGVDIA YIKIPNAGQM QPVKAFKIHN

KIWVIPERDT FTNPEEGDLN PPPEAKQVPV SYYDSTYLST

DNEKDNYLKG VTKLFERIYS TDLGRMLLTS IVRGIPFWGG

STIDTELKVI DTNCINVIQP DGSYRSEELN LVIIGPSADI

IQFECKSFGH EVLNLTRNGY GSTQYIRFSP DFTFGFEESL

EVDTNPLLGA GKFATDPAVT LAHELIHAGH RLYGIAINPN

RVFKVNTNAY YEMSGLEVSF EELRTFGGHD AKFIDSLQEN

EFRLYYYNKF KDIASTLNKA KSIVGTTASL QYMKNVFKEK

YLLSEDTSGK FSVDKLKFDK LYKMLTEIYT EDNFVKFFKV

LNRKTYLNFD KAVFKINIVP KVNYTIYDGF NLRNTNLAAN

FNGQNTEINN MNFTKLKNFT GLFEFYKLLC VRGIITSKTK

SLDKGYNKAL NDLCIKVN

<Sequence List15>
                                              (SEQ ID NO: 15)
MPVTINNFNY NDPIDNNNII MMEPPFARGT GRYYKAFKIT

DRIWIIPERY TFGYKPEDFN KSSGIFNRDV CEYYDPDYLN

TNDKKNIFLQ TMIKLFNRIK SKPLGEKLLE MIINGIPYLG

DRRVPLEEFN TNIASVTVNK LISNPGEVER KKGIFANLII

FGPGPVLNEN ETIDIGIQNH FASREGFGGI MQMKFCPEYV

SVFNNVQENK GASIFNRRGY FSDPALILMH ELIHVLHGLY

GIKVDDLPIV PNEKKFFMQS TDAIQAEELY TFGGQDPSII

TPSTDKSIYD KVLQNFRGIV DRLNKVLVCI SDPNININIY

KNKFKDKYKF VEDSEGKYSI DVESFDKLYK SLMFGFTETN

IAENYKIKTR ASYFSDSLPP VKIKNLLDNE IYTIEEGFNI

SDKNMEKEYR GQNKAINKQA YEEISKEHLA VYKIQMCKSV

R

<Sequence List16>
                                              (SEQ ID NO: 16)
TQIDLIRKKM KEAL
```

What is claimed is:

1. A cell penetrating peptide (CPP) comprising the amino acid sequence selected from the group consisting of SEQ ID NOs:1-3, wherein the peptide mediates transport of an active molecule into a cell.

2. A composition comprising the CPP according to claim 1, wherein the CPP is fused to a botulinum toxin recombinant protein.

3. The composition of claim 2, wherein the botulinum toxin recombinant protein is selected from the group consisting of serotypes A, B, C, D, E, F, and G.

4. The composition of claim 2, wherein the CPP is fused to a botulinum toxin recombinant protein light chain amino terminus, carboxyl terminus, or both termini.

5. The composition of claim 2, wherein the CPP is fused to the botulinum toxin recombinant protein by a peptide bond or a covalent bond.

6. The composition of claim 2, wherein the botulinum toxin recombinant protein comprises a botulinum toxin light chain consisting of SEQ ID NOs: 14 or 15, and a botulinum toxin heavy chain translocation region peptide consisting of SEQ ID NO:16.

7. The composition of claim 6, wherein the cell penetrating fused botulinum toxin recombinant protein further comprises at least one linker i) between the CPP and the botulinum toxin light chain, ii) between the botulinum toxin light chain and the translocation region peptide of a botulinum toxin heavy chain translocation region peptide, iii) between the botulinum toxin heavy chain translocation region peptide and the CPP, or iv) combinations thereof.

8. A cosmetic composition comprising the cell penetrating peptide fused to botulinum toxin recombinant protein according to claim 2.

9. The cosmetic composition of claim 8, further comprising a skin emulsifier.

10. The cosmetic composition of claim 8, wherein the skin emulsifier is glyceryl monostearate or cetyl alcohol.

11. The cosmetic composition of claim 9, wherein the skin emulsifier is at least 0.5 w/w % of the total weight of the composition.

12. The cosmetic composition of claim 8, wherein the cosmetic composition improves or prevents skin wrinkles.

\* \* \* \* \*